United States Patent
Ogawa et al.

(10) Patent No.: US 11,627,885 B2
(45) Date of Patent: Apr. 18, 2023

(54) BLOOD PRESSURE MEASUREMENT DEVICE AND BLOOD PRESSURE MEASUREMENT METHOD

(71) Applicant: Sharp Kabushiki Kaisha, Sakai (JP)

(72) Inventors: Rieko Ogawa, Sakai (JP); Yoshihisa Adachi, Sakai (JP); Yuki Edo, Sakai (JP); Ryota Tomizawa, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 392 days.

(21) Appl. No.: 16/772,188

(22) PCT Filed: Dec. 5, 2018

(86) PCT No.: PCT/JP2018/044802
§ 371 (c)(1),
(2) Date: Jun. 12, 2020

(87) PCT Pub. No.: WO2019/116996
PCT Pub. Date: Jun. 20, 2019

(65) Prior Publication Data
US 2021/0068678 A1 Mar. 11, 2021

(30) Foreign Application Priority Data
Dec. 15, 2017 (JP) .............................. JP2017-240930

(51) Int. Cl.
*A61B 5/021* (2006.01)
*A61B 5/00* (2006.01)

(52) U.S. Cl.
CPC ........ *A61B 5/02125* (2013.01); *A61B 5/7246* (2013.01)

(58) Field of Classification Search
CPC ............. A61B 5/02125; A61B 5/7246; A61B 2560/0247; A61B 5/0022; A61B 5/0077;
(Continued)

(56) References Cited

U.S. PATENT DOCUMENTS 10,292,662 B2 * 5/2019 Kirenko ................... G06T 7/11
2016/0338602 A1 11/2016 Oksala
(Continued)

FOREIGN PATENT DOCUMENTS

| CN | 105916436 A | 8/2016 |
| JP | 2015-054223 A | 3/2015 |

(Continued)

OTHER PUBLICATIONS

Official Communication issued in International Patent Application No. PCT/JP2018/044802, dated Feb. 26, 2019.

*Primary Examiner* — Jung Kim
(74) *Attorney, Agent, or Firm* — Keating & Bennett, LLP

(57) ABSTRACT

There is provided a technique configured to measure blood pressure with high accuracy. A pulse wave is acquired from each of a plurality of regions on a body surface of a subject, at least two regions are selected from among the plurality of regions in accordance with signal quality of the acquired pulse wave of each region, and blood pressure information is calculated with reference to pulse wave propagation information indicating pulse wave propagation between the at least two regions selected.

14 Claims, 10 Drawing Sheets

(58) Field of Classification Search
CPC ... A61B 5/1495; A61B 5/4842; A61B 5/6814; A61B 5/7257; G06T 2200/24; G06T 2207/10016; G06T 2207/10152; G06T 2207/20021; G06T 2207/20056; G06T 2207/30104; G06T 2207/30168; G06T 2207/30196; G06T 7/0012
See application file for complete search history.

(56) References Cited

U.S. PATENT DOCUMENTS

| | | |
|---|---|---|
| 2017/0164904 A1 | 6/2017 | Kirenko |
| 2018/0042486 A1 | 2/2018 | Yoshizawa et al. |

FOREIGN PATENT DOCUMENTS

| | | |
|---|---|---|
| JP | 2016-077426 A | 5/2016 |
| JP | 2016-190022 A | 11/2016 |
| JP | 2016-539697 A | 12/2016 |
| WO | 2016/163019 A1 | 10/2016 |

* cited by examiner

FIG.14
(a)
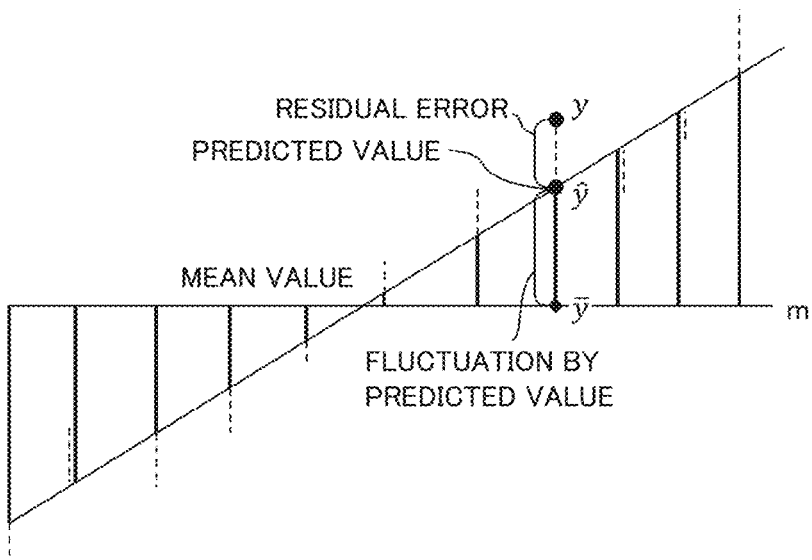
(b)
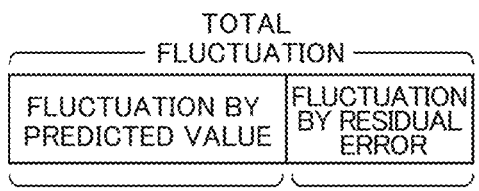
(c)
| RANK | FOREHEAD AREA REGION No. | CHEEK AREA REGION No. | FREEDOM DEGREE-ADJUSTED COEFFICIENT OF DETERMINATION |
|---|---|---|---|
| 1 | 6 | 22 | 0.84 |
| 2 | 8 | 13 | 0.77 |
| 3 | 1 | 19 | 0.67 |
| 4 | 8 | 20 | 0.61 |
| 5 | 8 | 17 | 0.54 |
| 6 | 7 | 22 | 0.52 |
| 7 | 8 | 19 | 0.50 |
| 8 | 4 | 22 | 0.47 |
| 9 | 7 | 19 | 0.44 |
| 10 | 1 | 17 | 0.42 |

BLOOD PRESSURE MEASUREMENT DEVICE AND BLOOD PRESSURE MEASUREMENT METHOD

TECHNICAL FIELD

An aspect of the present disclosure relates to a blood pressure measurement device and a blood pressure measurement method.

BACKGROUND ART

Non-contact blood pressure meters configured to measure blood pressure using a camera have been proposed (see, for example, PTL1). In these non-contact blood pressure meters, blood pressure is estimated from a time difference (pulse wave propagation time) between two sites (for example, the hand and the face) in an image.

CITATION LIST

Patent Literature

PTL 1: JP 2016-190022 A (published on Nov. 10, 2016)

SUMMARY OF INVENTION

Technical Problem

In order to estimate blood pressure using an image captured by a single camera, it is desirable to measure the blood pressure by calculating a pulse wave propagation time only from an image of the face. However, since the face is a limited small region, the distance traveled by the pulse wave is short, which makes it difficult to detect a change in the pulse wave propagation time accompanying a change in blood pressure. Accordingly, it is difficult to accurately measure blood pressure only from a facial image.

An aspect of the present disclosure has been conceived in view of the above-described circumstances, and an object of the present disclosure is to achieve a technique configured to measure blood pressure with high accuracy.

Solution to Problem

In order to solve the above problem, a blood pressure measurement device according to an aspect of the present disclosure includes: a pulse wave acquisition unit configured to acquire a pulse wave from each of a plurality of regions on a body surface of a subject; a region selection unit configured to select at least two regions from among the plurality of regions in accordance with signal quality of the pulse wave of each region acquired by the pulse wave acquisition unit; and a blood pressure information acquisition unit configured to calculate blood pressure information with reference to pulse wave propagation information indicating pulse wave propagation between the at least two regions selected by the region selection unit.

In order to solve the above problem, a blood pressure measurement method according to an aspect of the present disclosure includes: acquiring a pulse wave from each of a plurality of regions on a body surface of a subject; selecting at least two regions from among the plurality of regions in accordance with signal quality of the pulse wave of each region acquired by the acquiring of the pulse wave; and acquiring blood pressure information in which the blood pressure information is calculated with reference to pulse wave propagation information indicating pulse wave propagation between the at least two regions selected by the selecting of the at least two regions.

Advantage Effects of Invention

According to aspects of the present disclosure, blood pressure may be measured with high accuracy.

BRIEF DESCRIPTION OF DRAWINGS

FIGS. 14($a$) and ($b$) are diagrams illustrating a relationship between a fluctuation by estimated blood pressure and a fluctuation by a residual error relative to the mean blood pressure of measured blood pressure, and FIG. 14($c$) is a table illustrating rankings of optimal regions.

DESCRIPTION OF EMBODIMENTS

First Embodiment

Figure 1:
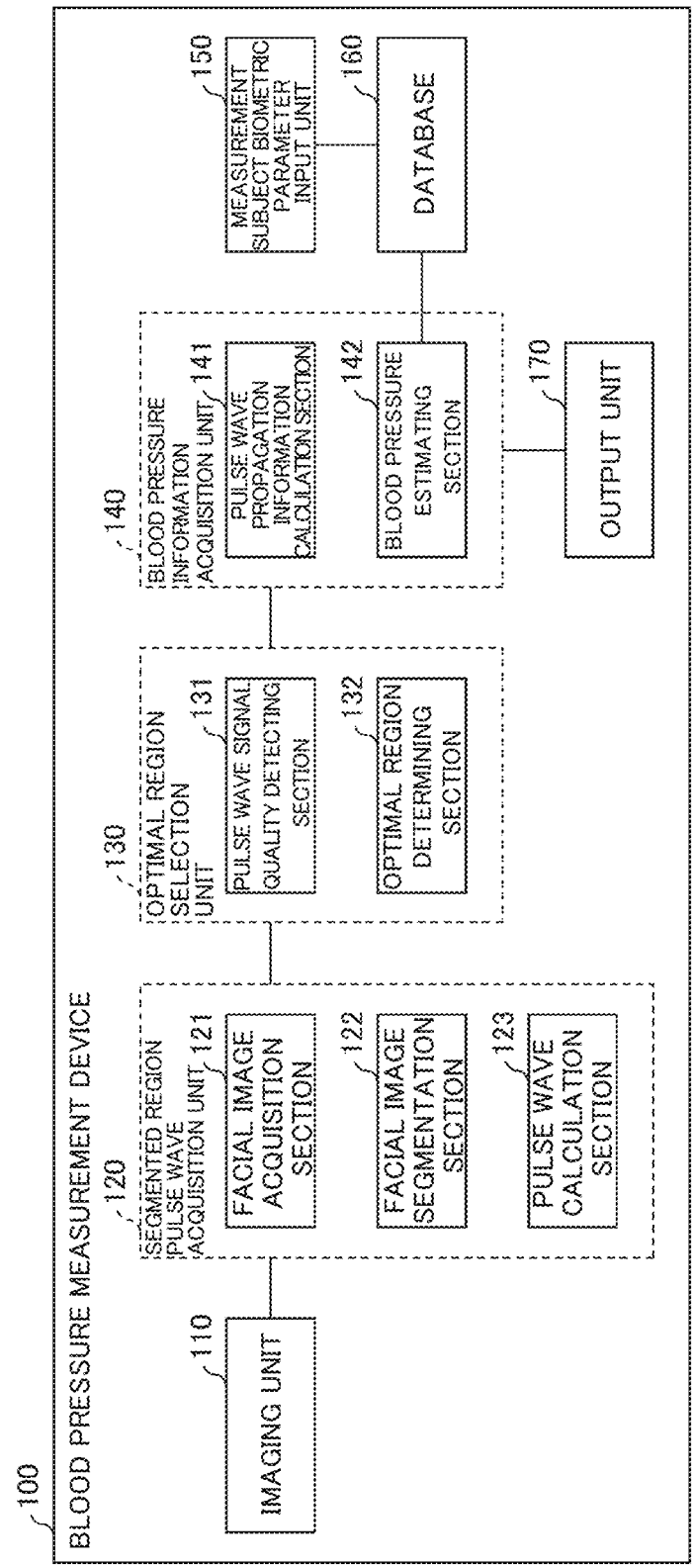
FIG. 1 is a block diagram illustrating a schematic constitution of a blood pressure measurement device 100 according to a first embodiment of the present disclosure.

Hereinafter, a first embodiment of the present disclosure will be described in detail. FIG. 1 is a block diagram illustrating a schematic constitution of a blood pressure measurement device 100 according to a first embodiment of the present disclosure. The blood pressure measurement device 100 is a non-contact blood pressure measurement device configured to measure blood pressure from an image of the face of a blood pressure measurement subject (subject).

Configuration of Blood Pressure Measurement Device 100

As illustrated in FIG. 1, the blood pressure measurement device 100 includes a segmented region pulse wave acquisition unit (pulse wave acquisition unit) 120, an optimal region selection unit (region selection unit) 130, and a blood pressure information acquisition unit 140. The blood pressure measurement device 100 includes an imaging unit 110, a measurement subject biometric parameter input unit 150, a database 160, and an output unit 170.

The segmented region pulse wave acquisition unit 120, the optimal region selection unit 130, and the blood pressure information acquisition unit 140 are configured as functional units of a controller that controls respective portions of the blood pressure measurement device 100 by, for example, at least one processor (such as a central processing unit (CPU)) executing a program stored in at least one memory (such as a random-access memory (RAM) or a read-only memory (ROM)).

Configuration of Segmented Region Pulse Wave Acquisition Unit 120

The segmented region pulse wave acquisition unit 120 includes a facial image acquisition section 121, a facial image segmentation section 122, and a pulse wave calculation section 123.

From a captured image of the subject, the facial image acquisition section 121 extracts and acquires the face of the subject contained in the captured image. The facial image acquisition section 121 may perform face tracking on a moving image containing the face of the subject to extract the facial region of the subject for each fixed frame. The facial image acquisition section 121 may have a configuration in which the subject can be identified by image recognition with reference to the acquired image of the face of the subject.

Figure 2:
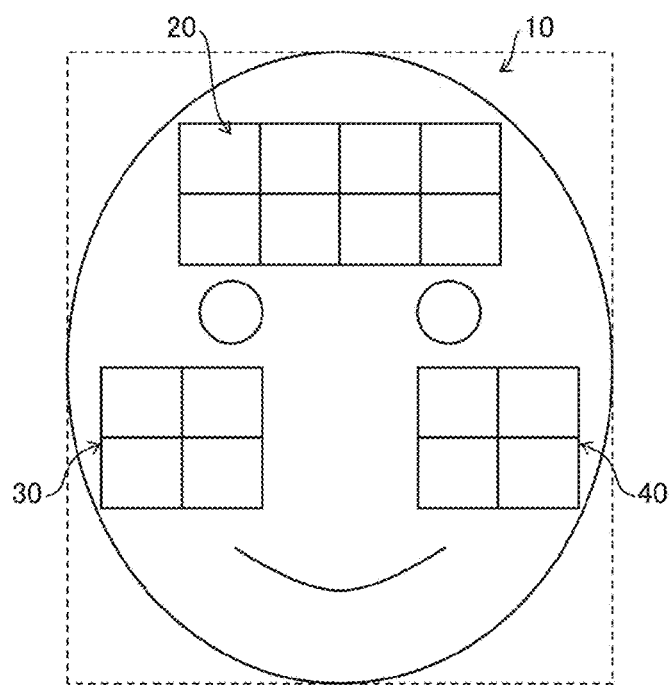
FIG. 2 is a diagram illustrating an example of an image of the face of a subject segmented into a plurality of regions.

The facial image segmentation section 122 segments the image of the face of the subject acquired by the facial image acquisition section 121 into a plurality of regions. FIG. 2 illustrates an example of an image 10 of the face of the subject segmented into a plurality of regions by the facial image segmentation section 122. As illustrated in FIG. 2, with respect to the acquired image 10 of the face of the subject, the facial image segmentation section 122 segments a forehead area 20 on the upper side of the eye into two segments vertically and into four segments horizontally, and also segments each of a right cheek area 30 and a left cheek area 40 on the lower side of the eye into two segments vertically and into two segments horizontally. Note that the segmentation method used by the facial image segmentation section 122 is not limited thereto. Each of the forehead area 20 and the cheek areas 30, 40 may be segmented into at least two left and right segments. In this manner, the facial image segmentation section 122 segments each of the plurality of specific areas in the image of the face of the subject into a plurality of regions.

The pulse wave calculation section 123 calculates a pulse wave in each region of the image segmented into the plurality of regions by the facial image segmentation section 122 with reference to the image of the region. To be specific, the pulse wave calculation section 123 calculates a pulse wave for each region of each of the forehead area 20 segmented into two segments vertically and four segments horizontally and the left and right cheek areas 30, 40 each segmented into two segments vertically and two segments horizontally.

First, the pulse wave calculation section 123 acquires a signal of a change in time of the pixel average of luminance values of each of colors (R, G, and B when captured by an RGB camera) of each region. The pulse wave calculation section 123 performs independent component analysis on the acquired signal, and extracts the same number of independent components as the number of colors. The pulse wave calculation section 123 uses a digital band-pass filter from 0.75 to 4.0 Hz, for example, for these independent components to remove both a low frequency component and a high frequency component from the signal. The pulse wave calculation section 123 performs the fast Fourier transform on the signal having passed through the band-pass filter, and calculates a power spectrum of the frequency. The pulse wave calculation section 123 calculates a peak (Pulse Rate (PR)) of the power spectrum at from 0.75 to 4.0 Hz, and detects the independent component having the highest peak value as a pulse wave signal by comparing with peak values of the independent components.

As described above, the segmented region pulse wave acquisition unit 120 functions as a pulse wave acquisition unit configured to acquire pulse waves from each of the plurality of regions where the pulse waves can be detected on the body surface of the subject. In the present embodiment, the segmented region pulse wave acquisition unit 120 acquires pulse waves from a captured image of the subject, with reference to a change in time of the pixel average of the luminance values of each color in each of the regions on the subject's body surface. The segmented region pulse wave acquisition unit 120 is not limited to the above-discussed operations, and may acquire the pulse waves by using contact sensors being mounted in contact with each of the plurality of regions where the pulse waves can be detected on the subject's body surface.

Configuration of Optimal Region Selection Unit 130

The optimal region selection unit 130 includes a pulse wave signal quality detecting section 131 and an optimal region determining section 132.

The pulse wave signal quality detecting section 131 detects signal quality of pulse waves in each of the regions calculated by the pulse wave calculation section 123. The pulse wave signal quality detecting section 131 detects a Signal-to-Noise Ratio (SNR) of the pulse wave signal calculated by the following method, for example, as pulse wave signal quality.

Figure 3:
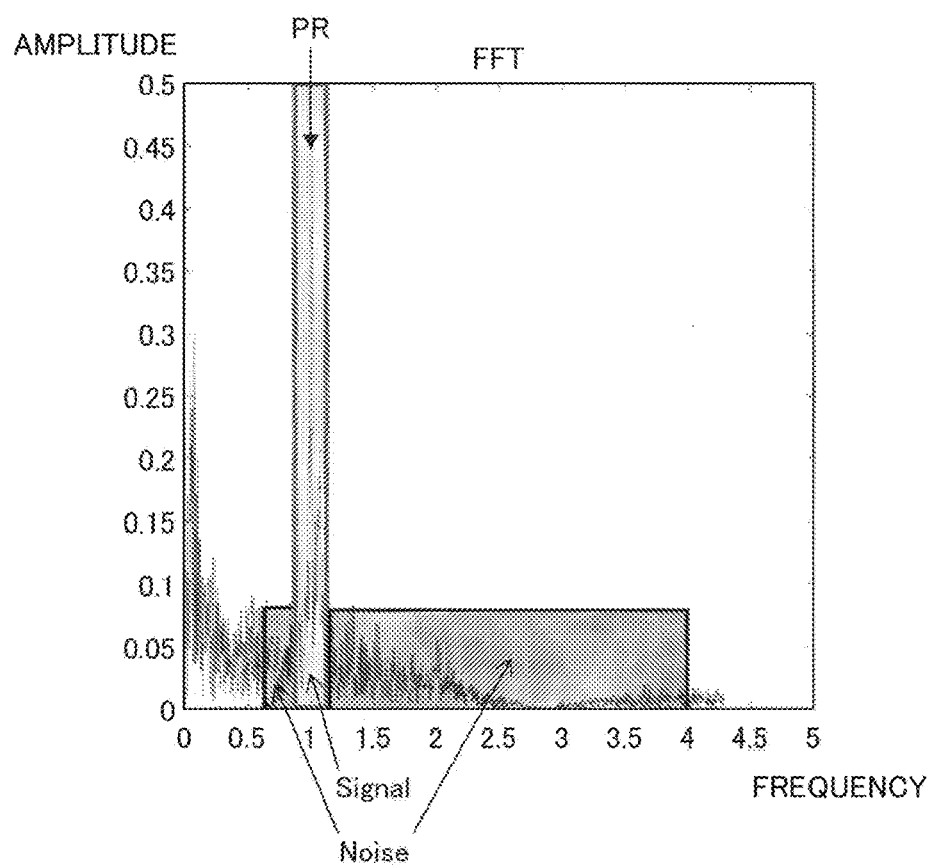
FIG. 3 is a diagram illustrating a power spectrum of a frequency of a pulse wave signal.

FIG. 3 is a power spectrum of the frequency of a pulse wave signal. Since the pulse wave is a wave that is transmitted to an artery by the pumping action of the heart, the pulse wave signal has a fixed period in accordance with the heartbeat, and the peak can be seen at about 1 Hz when frequency analysis is performed on the pulse wave signal. Using this, as illustrated in FIG. 3, the pulse wave signal quality detecting section 131 calculates the SNR in which a power sum of PR±0.05 Hz in the frequency power spectrum of the pulse wave signal is taken as a signal, and a power sum from 0.75 to 4.0 Hz excluding the signal band as noise. Note that the bandwidths of the signal and noise are not limited thereto. The method for detecting the pulse wave signal quality is a known method (for reference: DistancePPG: Robust non-contact vital signs monitoring using a camera), and other methods may be used as appropriate.

Figure 4:
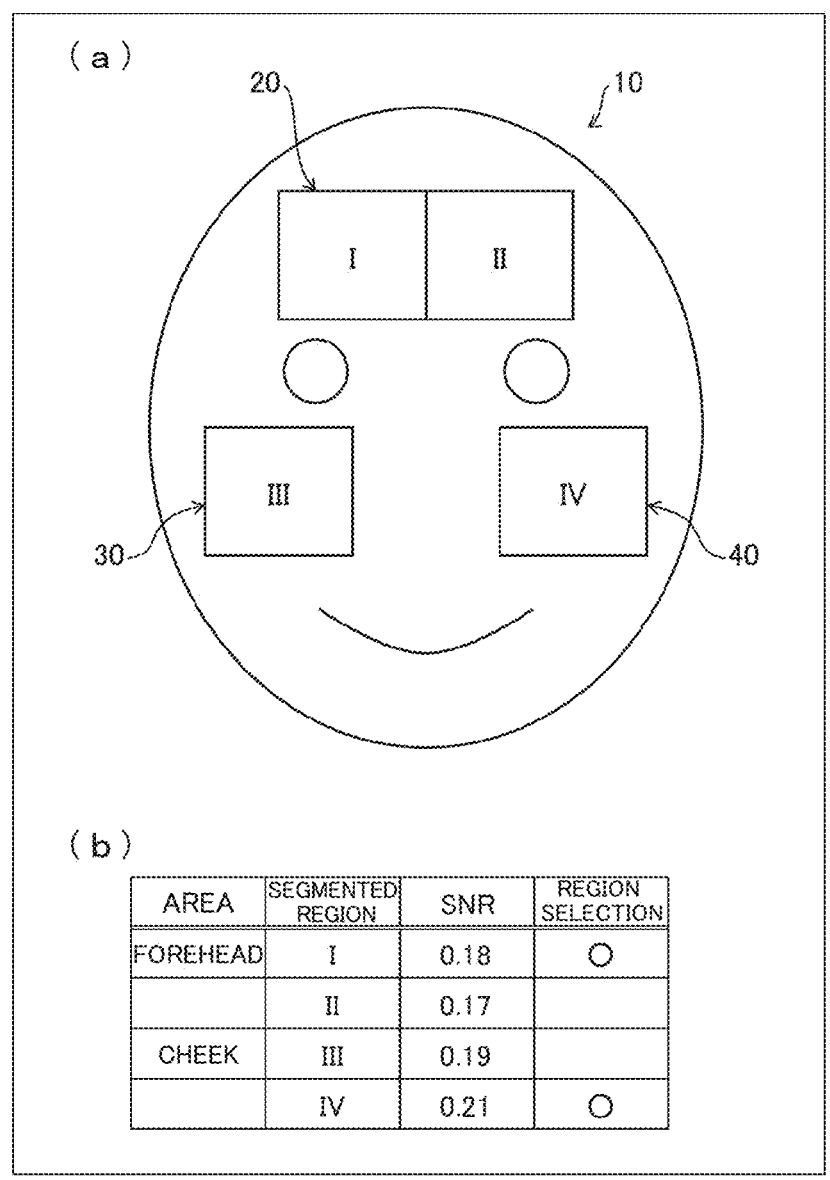
FIG. 4($a$) illustrates an example of segmented regions, and FIG. 4($b$) is a diagram illustrating an SNR of each segmented region.

The optimal region determining section 132 selects at least two regions in accordance with the signal quality having been detected by the pulse wave signal quality detecting section 131. FIG. 4(*a*) illustrates the positions corresponding to segmented regions I to VI in a case where, for example, the forehead area 20 is segmented into two segments horizontally, and a cheek area is segmented into the right cheek area 30 and the left cheek area 40. FIG. 4(*b*) is a table illustrating a method for determining an optimal region based on the SNR of each of the segmented regions I to IV detected by the pulse wave signal quality detecting section 131. As for the face segmentation, the region selection may be carried out based on the pulse wave signal quality only in any one of the areas (in the present embodiment, a first area (forehead area) or a second area (cheek area)). In a case where neither of the two areas is further segmented (in a case where the number of regions for signal acquisition is only two in the overall face), a selection may be carried out in which pulse wave propagation information is not output when the pulse wave signal quality of any one or both of the regions is lower than a set numeric value.

As illustrated in FIGS. 4(a) and (b), the optimal region determining section 132 selects a region having the highest SNR in each of the forehead area 20 and the cheek areas 30, 40 based on the SNR of each of the segmented regions I to IV having been detected by the pulse wave signal quality detecting section 131. In the example illustrated in FIG. 4(b), the SNR is high in the segmented region I in the forehead area 20, and is high in the segmented region IV in the cheek areas 30 and 40. The optimal region determining section 132 determines the segmented region I and the segmented region IV as optimal regions used for a blood pressure estimation.

As described above, the optimal region determining section 132 selects an optimal region for each of the plurality of specific areas having been preset in the image of the face of the subject, and then determines, as optimal regions, at least two regions having high pulse wave signal quality among the optimal regions in the specific areas. As described above, the optimal region determining section 132 selects one region in which the pulse wave signal quality is optimal to be used for the blood pressure estimation in each of the forehead area 20 and the cheek areas 30 and 40, which are the plurality of preset specific areas in the image of the face of the subject. Then, the blood pressure estimation is performed between the optimal regions for each specific area. Thus, even in a limited small area of the face, a fixed pulse wave propagation distance may be taken, thereby making it possible to estimate blood pressure with high accuracy.

A velocity v at which a pulse wave propagates in the blood vessel is represented by Equation (1) given below (Moens-Korteweg equation) when the Young's modulus of the blood vessel is E, the blood vessel wall thickness is a, the blood vessel diameter is R, and the blood density is ρ.

[Equation 1]

$$v = \sqrt{\frac{Ea}{2R\rho}} \quad (1)$$

The Young's modulus of the blood vessel E varies exponentially with respect to blood pressure P, and in the case where the Young's modulus of the blood vessel when P is equal to 0 is taken as $E_0$, the Young's modulus of the blood vessel E is represented by Equation (2) given below. Note that γ is a constant dependent on the blood vessel.

[Equation 2]

$$E = E_0 e^{\gamma P} \quad (2)$$

When a pulse wave propagation time is taken as T, and the length of a blood vessel pathway is taken as L, the length of the blood vessel pathway L is represented by Equation (3) given below.

[Equation 3]

$$\downarrow L = vT \quad (3)$$

It has been known that Equation (4) given below is derived from Equation (1) to Equation (3) discussed above, and that the pulse wave propagation time T has a correlation with the blood pressure P when the length of the blood vessel pathway is fixed.

[Equation 4]

$$P = \frac{1}{\gamma} \left( \ln \frac{1}{T^2} + \ln \frac{2R\rho L^2}{E_0 a} \right) \quad (4)$$

Configuration of Blood Pressure Information Acquisition Unit 140

The blood pressure information acquisition unit 140 includes a pulse wave propagation information calculation section 141 and a blood pressure estimating section 142.

Figure 5:
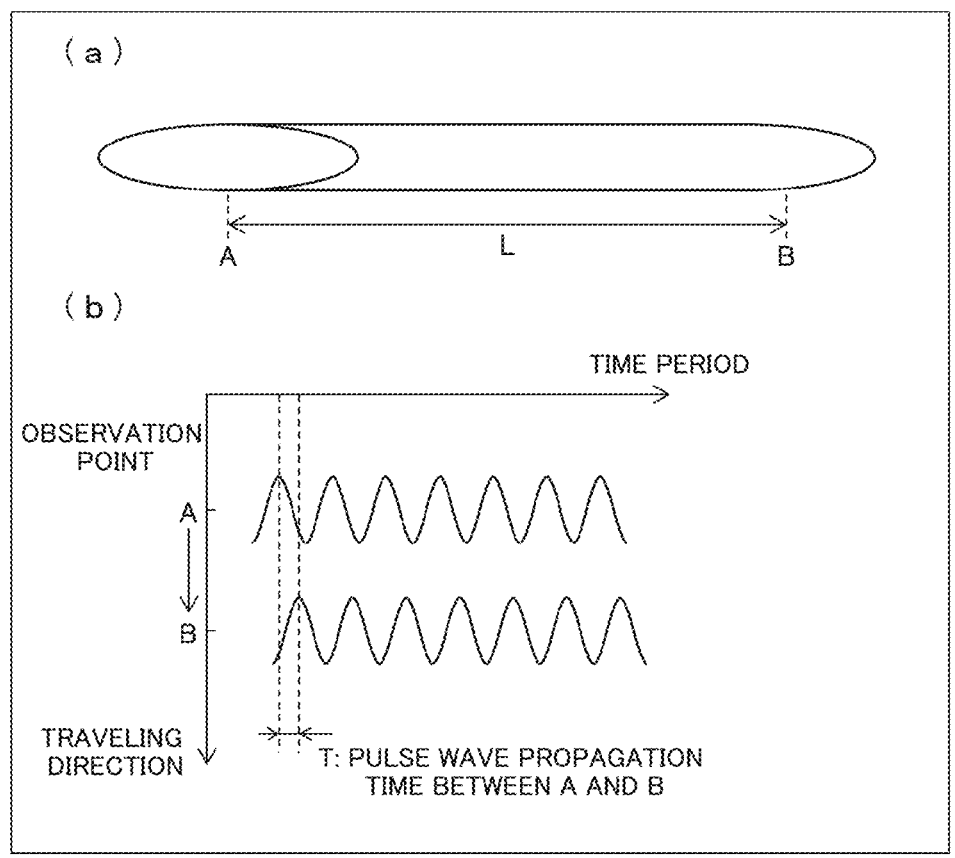
FIGS. 5($a$) and ($b$) are image diagrams with regard to measurement of a pulse wave propagation time.

The pulse wave propagation information calculation section 141 calculates pulse wave propagation information indicating pulse wave propagation between at least two regions selected by the optimal region selection unit 130. FIGS. 5(a) and (b) are image diagrams with regard to measurement of a pulse wave propagation time. The pulse wave propagation information calculation section 141 calculates a time in which a pulse wave propagates from a region A to a region B, where the length of a blood vessel pathway is L. As illustrated in FIG. 5(b), for example, the pulse wave propagation information calculation section 141 calculates a pulse wave propagation time by calculating a time difference (shift width) in which a cross-correlation coefficient between waveforms is greatest when a pulse wave obtained from the region selected by the optimal region determining section 132 is shifted in a time direction. The pulse wave propagation information calculation section 141 may calculate a finer time difference by interpolation such as spline interpolation. The pulse wave propagation information calculation section 141 may calculate the pulse wave propagation time by detecting a characteristic point such as a maximum value of the pulse wave obtained from the region selected by the optimal region determining section 132 or a rising point of the stated pulse wave, and calculating the time difference thereof.

The blood pressure estimating section 142 calculates blood pressure information, which is estimated blood pressure of the subject, by using Equation (4) discussed above with reference to the pulse wave propagation information having been calculated by the pulse wave propagation information calculation section 141. The blood pressure estimating section 142 selects a blood pressure estimation formula corresponding to the measurement subject biometric parameter input via the measurement subject biometric parameter input unit 150. The blood pressure estimating section 142 uses the selected blood pressure estimation formula to calculate estimated blood pressure based on the pulse wave propagation time calculated in the pulse wave propagation information calculation section 141. It is sufficient that the blood pressure estimating section 142 is configured to use the pulse wave propagation time obtained above as at least one of explanatory variables in estimating the blood pressure in which the blood pressure is taken as an objective variable, and in addition, an amount of characteristics or the like obtained from a pulse wave form having been obtained from a screen image of a face may also be used in combination therewith.

With regard to the estimation formula used for the blood pressure estimation, as an explanatory variable, only one pulse wave propagation time, or only the combination use of one pulse wave propagation time and the amount of characteristics obtained from the pulse wave form has been described thus far; however, the explanatory variable is not limited thereto, and a blood pressure estimation formula using a plurality of pulse wave propagation times as an explanatory variable may be employed. In determining the estimation formula, regression analysis using a least square method, an estimation in which the suppression of over learning is taken into consideration by LASSO with L1 regularization introduced, and the like may be performed.

The imaging unit 110 captures an area including the face of the subject whose blood pressure is to be measured. The imaging unit 110 may be configured to be integrally provided in the blood pressure measurement device 100, may be an in-camera of a smartphone, may be a camera mounting on a watching robot, or the like. In such a configuration that the imaging unit 110 is separate from the blood pressure measurement device 100, the imaging unit 110 may be configured to communicate with the blood pressure measurement device 100, for example, via wireless communication, and supply the captured image to the blood pressure measurement device 100.

The imaging unit 110 is a camera in which an image sensor of CMOS, CCD, or the like is combined with a lens, and includes a color filter suitable for observing an increase and decrease in the amount of blood such as a color filter of Bayer arrangement of RGB, which is generally used, a color filter of RGBCy in which a color filter of Cy (Cyan) is added to a color filter of RGB, a color filter of RGBIR in which a color filter of IR (near infrared) is added to a color filter of RGB, or the like. The color filter is not limited to the filter described above, and only an IR color filter may be included, for example.

The imaging unit 110 may be, when the subject is captured therewith, configured to display, for example, an image capturing area on a display section of a smartphone, and a frame, into which the face of the subject is to be fit, that is set within the image capturing area. In a case where the subject fits his or her face into the set frame and the image is captured in a state of the camera and the face being fixed, the facial image acquisition section 121 is able to extract the face of the subject from the image without performing face tracking.

The imaging unit 110 may be configured to capture a static image of an area including the face of the subject every predetermined time (for example, every 0.1 seconds), or may be configured to capture a moving image of the area including the face of the subject.

The measurement subject biometric parameter input unit 150 receives input of biometric parameters by a user. The user inputs measurement subject biometric parameters such as gender, age, and BMI via the measurement subject biometric parameter input unit 150. The user may be the subject himself or herself whose blood pressure is to be measured, or may be a third party prompting the subject to measure the blood pressure.

Figure 6:
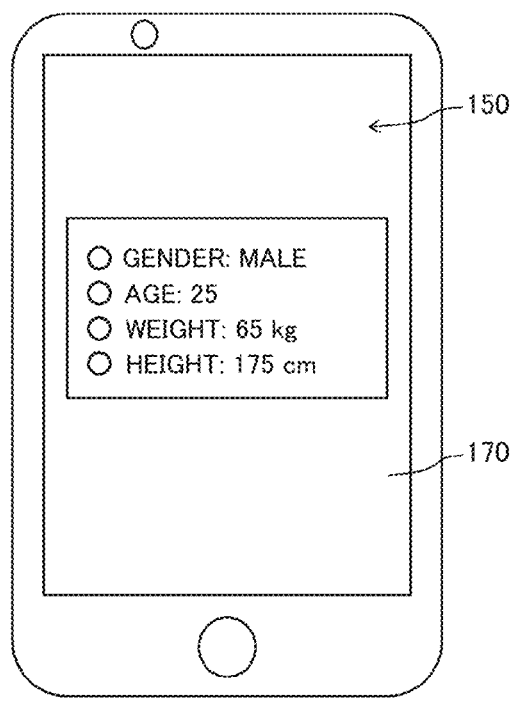
FIG. 6 is a diagram illustrating an example of a measurement subject biometric parameter input unit.

FIG. 6 is a diagram illustrating an example of the measurement subject biometric parameter input unit 150. As illustrated in FIG. 6, the measurement subject biometric parameter input unit 150 may be configured to include, for example, a parameter input screen displayed on a display section of a smartphone, and a touch panel arranged being superimposed on the display section.

The measurement subject biometric parameter input unit 150 may employ various known user interfaces as long as the subject's parameters such as gender, age, weight, height and the like to be referenced when the blood pressure estimating section 142 selects an estimation formula used for estimating the blood pressure are allowed to be input.

Although not illustrated in the drawings, for example, the blood pressure measurement device 100 may be so configured as to be able to request the user to input the biometric parameters by displaying the message on the display section, outputting the voice message from a speaker, or the like.

Figure 7:
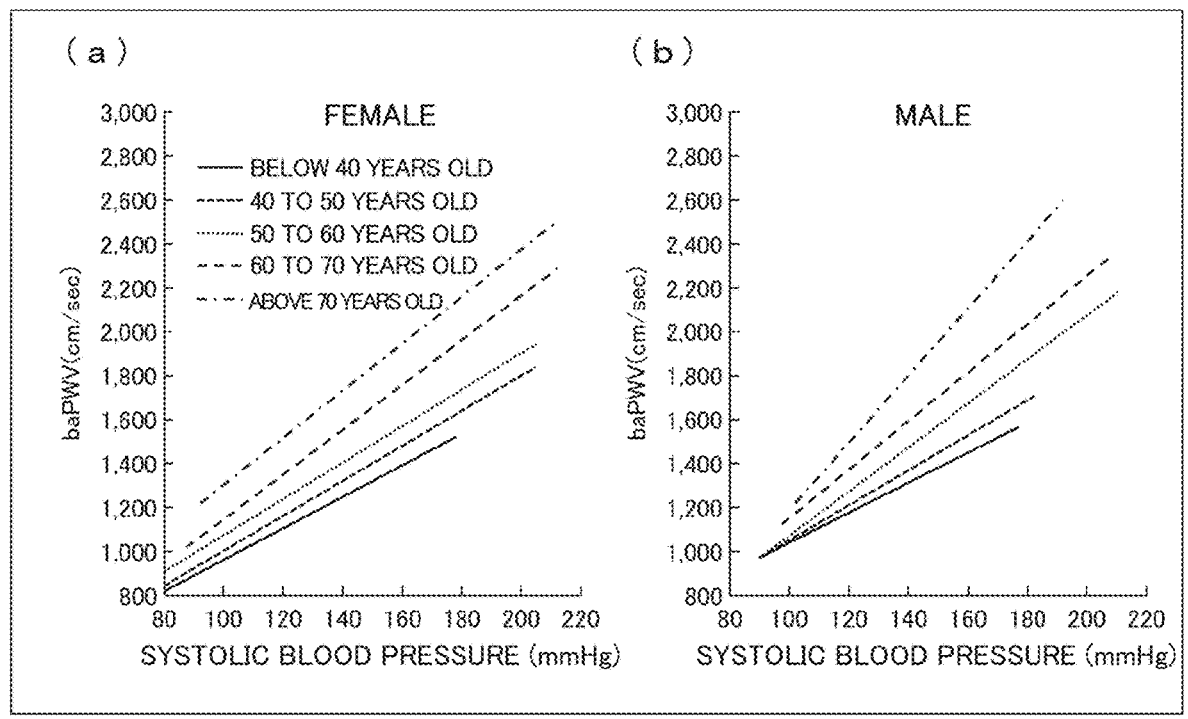
FIG. 7 is a diagram illustrating a relationship of gender, age, and systolic blood pressure.

FIG. 7 is a diagram illustrating a known relationship of gender, age, and systolic blood pressure (reference book: Learn PWV and Examine by PWV; Nakayama Shoten Co., Ltd.). As illustrated in FIG. 7, it is reported that systolic blood pressure varies in accordance with gender and age. The database 160 stores blood pressure estimation formulas for each of the regions segmented by the facial image segmentation section 122, where the formulas are standard ones for each of the biometric parameters such as gender, age, BMI and the like.

The database 160 may be configured to be integrally included in the blood pressure measurement device 100, or may be configured to be separate from the blood pressure measurement device 100. The database 160 may be configured to communicate with the blood pressure measurement device 100, for example, via wireless communication, and supply, to the blood pressure measurement device 100, the blood pressure estimation formulas of individual biometric parameters between the respective regions.

Figure 8:
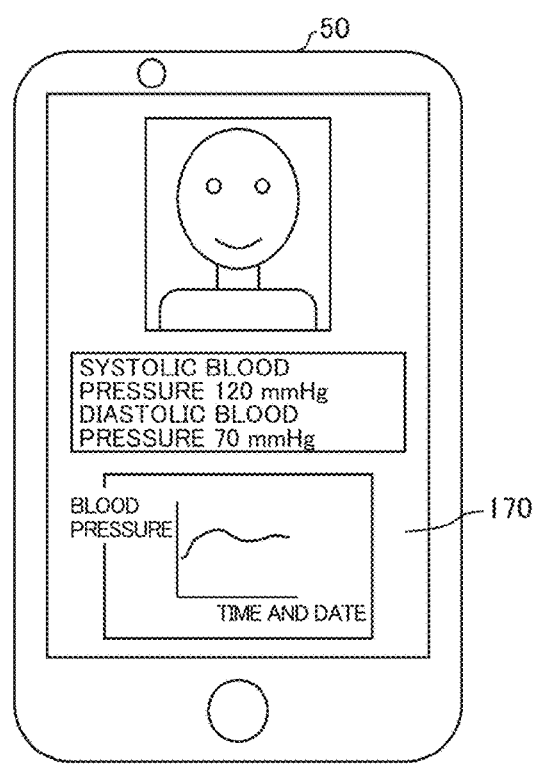
FIG. 8 is a diagram illustrating an example of an output unit.

The output unit 170 outputs estimated blood pressure of the subject calculated by the blood pressure estimating section 142. FIG. 8 is a diagram illustrating an example of the output unit 170. As illustrated in FIG. 8, for example, the output unit 170 causes a display section of a smartphone to display a blood pressure value estimated by the blood pressure estimating section 142. The output unit 170 may display an image of the subject's face and an avatar of the subject for identifying the subject, along with systolic blood pressure and diastolic blood pressure estimated by the blood pressure estimating section 142. In addition, the output unit 170 may display a blood pressure fluctuation graph indicating daily fluctuations in blood pressure, intra-day fluctuations in blood pressure, or the like of the subject. Although not illustrated in the drawings, the blood pressure measurement device 100 may be provided with a storage unit configured to store the estimated blood pressure by the blood pressure estimating section 142, and the output unit 170 may be configured to generate and output a blood pressure fluctuation graph indicating daily blood pressure fluctuations and intra-day blood pressure fluctuations with reference to the record of blood pressure of the subject stored in the storage unit.

The output unit 170 may output, by voice output, the estimated blood pressure of the subject calculated by the blood pressure estimating section 142 in such a manner that the subject can confirm the estimated blood pressure.

Process Flow of Blood Pressure Measurement Device 100

Figure 9:
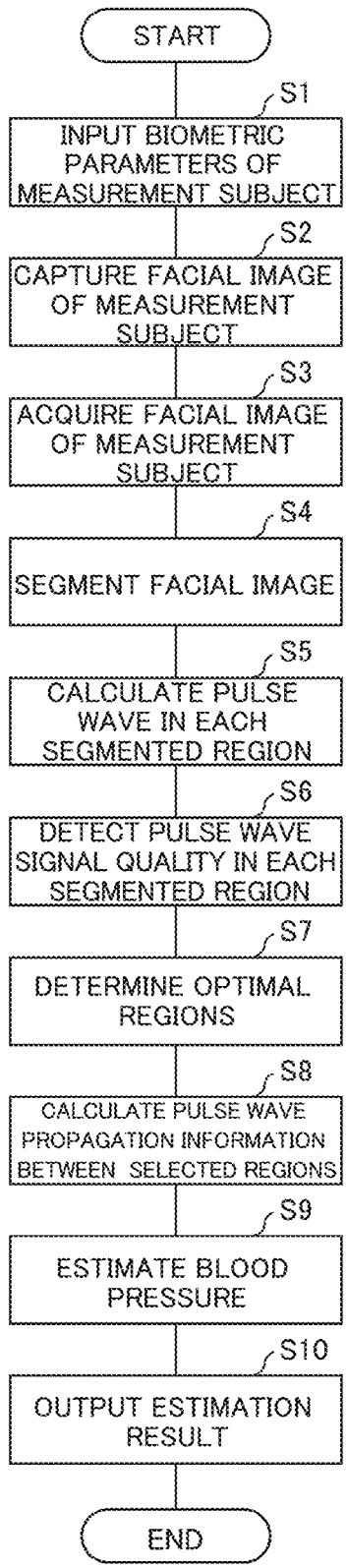
FIG. 9 is a flowchart illustrating a process flow of a blood pressure measurement device according to the first embodiment.

FIG. 9 is a flowchart illustrating a process flow of the blood pressure measurement device 100.

Step S1

For example, when the blood pressure measurement is started by operation of a power supply button (not illustrated), a blood pressure measurement start button (not illustrated), or the like, the device first prompts a user to input biometric parameters of the subject via the measurement subject biometric parameter input unit 150, and receives the input of the biometric parameters of the measurement subject by the user.

Step S2

An image including the face of the subject is captured by the imaging unit 110.

Step S3

With the function of the facial image acquisition section 121, an image of the face of the subject is acquired from the captured image by the imaging unit 110.

Step S4

With the function of the facial image segmentation section 122, the image of the face of the subject acquired by the facial image acquisition section 121 is segmented into a plurality of regions.

Step S5

With the function of the pulse wave calculation section 123, a pulse wave in each region segmented by the facial image segmentation section 122 is calculated with reference to the image of the region.

Step S6

With the function of the pulse wave signal quality detecting section 131, signal quality of pulse waves in each of the regions calculated by the pulse wave calculation section 123.

Step S7

With the function of the optimal region determining section 132, at least two regions are determined in accordance with the pulse wave signal quality having been detected by the pulse wave signal quality detecting section 131.

Step S8

With the function of the pulse wave propagation information calculation section 141, pulse wave propagation information between at least two regions determined by the optimal region determining section 132 is calculated.

Step S9

With the function of the blood pressure estimating section 142, a blood pressure value of the subject is calculated and blood pressure information including the blood pressure value is acquired, with reference to the pulse wave propagation information between the at least two regions calculated by the pulse wave propagation information calculation section 141.

Step S10

With the function of the output unit 170, an estimation result of the blood pressure estimating section 142 is output in such a manner that the subject can confirm the estimated blood pressure.

As described above, with the blood pressure measurement device 100 according to the present embodiment, an image of the face of a subject whose blood pressure is to be measured is segmented into a plurality of regions; then, pulse waves of each of the segmented regions are calculated, and at least two regions are selected in accordance with the pulse wave signal quality in each region so as to calculate the blood pressure in accordance with the pulse wave propagation information between the selected regions. When the image of the face is segmented into a plurality of segments, the image of the face is segmented into a forehead area 20, a right cheek area 30, and a left cheek area 40, which are located on the upper and lower sides and right and left sides of the face, and optimal regions are selected from the respective areas to calculate a pulse wave propagation time between the selected regions. Thus, even from a facial image, which is a limited small region, it is possible to take a fixed pulse wave propagation distance between the forehead and the cheek. This makes it possible to take as long a pulse wave propagation time as possible, and suppress a measurement error of the pulse wave propagation time.

Since the forehead area 20 is segmented into two or more regions on the right and left, and the cheek area is segmented into the right cheek area 30 and the left cheek area 40, regions having better pulse wave signal quality may be selected. In addition, since each area is segmented into smaller regions, and the pulse wave is acquired from each region, it is also possible to shorten a time difference within the region in comparison with a case where the pulse wave is acquired in each of the whole area of the forehead, cheek, and the like. Thus, the pulse wave propagation time between the regions may also be more accurately determined, and the estimation accuracy of the blood pressure may be enhanced.

Since an optimal region is selected every time the blood pressure is measured, an optimal blood pressure estimation may be performed in accordance with an imaging environment at the time of each blood pressure measurement even in an imaging environment in which external light is not uniform, even from an image in which not all of the face is clearly captured, or the like. By selecting optimal regions every time the blood pressure is to be measured, it is possible to estimate blood pressure while taking into consideration personal differences such as facial contours. The facial image segmentation is not limited to the configuration in which the facial image is segmented into the forehead area 20 and the cheek areas 30 and 40, and the facial image may be segmented into a distal area and a proximal area.

In the present embodiment, a case has been described in which a pulse wave is calculated from an image of the face of a subject captured by the imaging unit 110. However, no such limitation is intended, and a configuration may be possible in which biometric information including pulse waves is acquired from a plurality of contact sensors attached to respective areas of the face. In this case, the plurality of contact sensors are classified for each area, and a signal having high quality is selected among the signals obtained from the contact sensor in the area. The contact sensors and the images may be used in combination.

Second Embodiment

A second embodiment of the disclosure will be described below. Note that, for convenience of explanation, components having the same functions as those described in the first embodiment will be denoted by the same reference signs, and descriptions of those components will be omitted.

Figure 10:
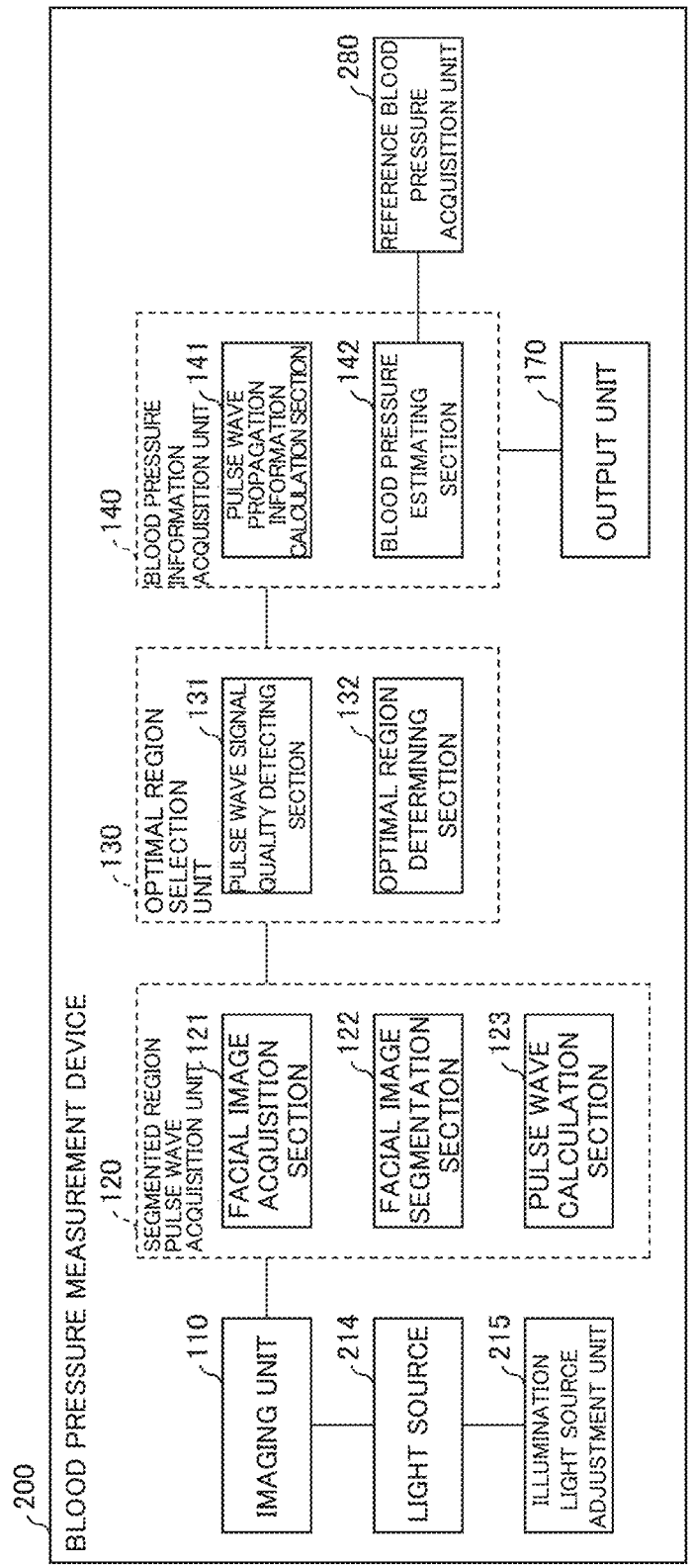
FIG. 10 is a block diagram illustrating a schematic constitution of a blood pressure measurement device 200 according to a second embodiment.

FIG. 10 is a block diagram illustrating a schematic constitution of a blood pressure measurement device 200 according to the second embodiment. As illustrated in FIG. 10, the blood pressure measurement device 200 differs in configuration from the blood pressure measurement device 100 according to the first embodiment in that the device includes a light source (illumination light source) 214, an illumination light source adjustment unit 215 and a reference blood pressure acquisition unit 280, but does not include the measurement subject biometric parameter input unit 150 and the database 160.

The light source 214 emits illumination light to illuminate the face of the subject when capturing an image by an imaging unit 110. The light source is not limited to visible light, and may be infrared light.

When an image is captured by the imaging unit 110, the illumination light source adjustment unit 215 adjusts light emission intensity of the light source 214 configured to emit illumination light for capturing the image including an image of the face of the subject. The illumination light source adjustment unit 215 is able to adjust the light emission intensity of the illumination light emitted by the light source 214 to obtain a fixed level of pulse wave signal quality even in different image capturing environments. Although not illustrated in the drawings, the illumination light source adjustment unit 215 may include, for example, an exposure meter to measure the brightness of the light illuminating the face of the subject, and may adjust the light emission intensity of the light source 214 in accordance with the measurement result. The illumination light source adjustment unit 215 may adjust the light emission intensity of the light source 214 in accordance with the brightness of the face of the subject measured at the previous time of image capturing by the imaging unit 110, for example.

The reference blood pressure acquisition unit 280 acquires the measured blood pressure of the subject at the same timing as that of the capturing of the image including the image of the face of the subject by the imaging unit 110. The reference blood pressure acquisition unit 280 may include, for example, a cuff-type blood pressure meter to acquire the measured blood pressure (reference blood pressure) of the subject obtained from the cuff-type blood pressure meter. The reference blood pressure acquisition unit 280 may be configured to include an invasive blood pressure meter using a catheter.

The reference blood pressure acquisition unit 280 may be configured to measure the measured blood pressure in the case where, for example, the subject is a subject whose blood pressure is measured for the first time. The reference blood pressure acquisition unit 280 may be configured to be able to prompt the subject to measure the measured blood pressure for each fixed period (for example, three months).

A blood pressure estimating section 142 uses pulse wave propagation information between at least two regions determined by an optimal region determining section 132 and the measured blood pressure acquired by the reference blood pressure acquisition unit 280 to create a blood pressure estimation formula corresponding to the subject. The blood pressure estimating section 142 stores the created blood pressure estimation formula associated with the subject until the subject measures his or her reference blood pressure next time. As discussed above, by measuring the reference blood pressure for each fixed period to create a blood pressure estimation formula corresponding to the subject, it is possible to deal with a change in blood vessel condition of the subject and maintain the blood pressure estimation accuracy in a high accuracy state.

The blood pressure estimating section 142 may create an estimation formula by using, for example, a plurality of data sets of the pulse wave propagation information and the reference blood pressure.

The blood pressure estimating section 142 estimates the blood pressure of the subject by using the estimation formula created at the time of calibration in which the estimation formula is created with reference to the reference blood pressure. The blood pressure estimating section 142 uses the estimation formula created at the time of calibration over a fixed period (for example, three months), and estimates the blood pressure without performing the calibration when the subject measures his or her blood pressure during that above period. The blood pressure estimating section 142 may be configured to give, to the subject, a message prompting the subject to perform the calibration when the subject has measured his or her blood pressure for the first time after the fixed period elapsed.

As described above, in the blood pressure measurement device 200, since the calibration is performed for each fixed period and for each subject to create a blood pressure estimation formula based on the measured blood pressure, it is possible to estimate the blood pressure suited to each subject and to estimate the blood pressure from the facial image with high accuracy. Thus, it is possible to estimate the blood pressure while taking into account personal differences such as facial contours and positions of the blood vessels.

Third Embodiment

A third embodiment of the disclosure will be described below. Note that, for convenience of explanation, components having the same functions as those described in the first or second embodiment will be denoted by the same reference signs, and descriptions of those components will be omitted.

Figure 11:
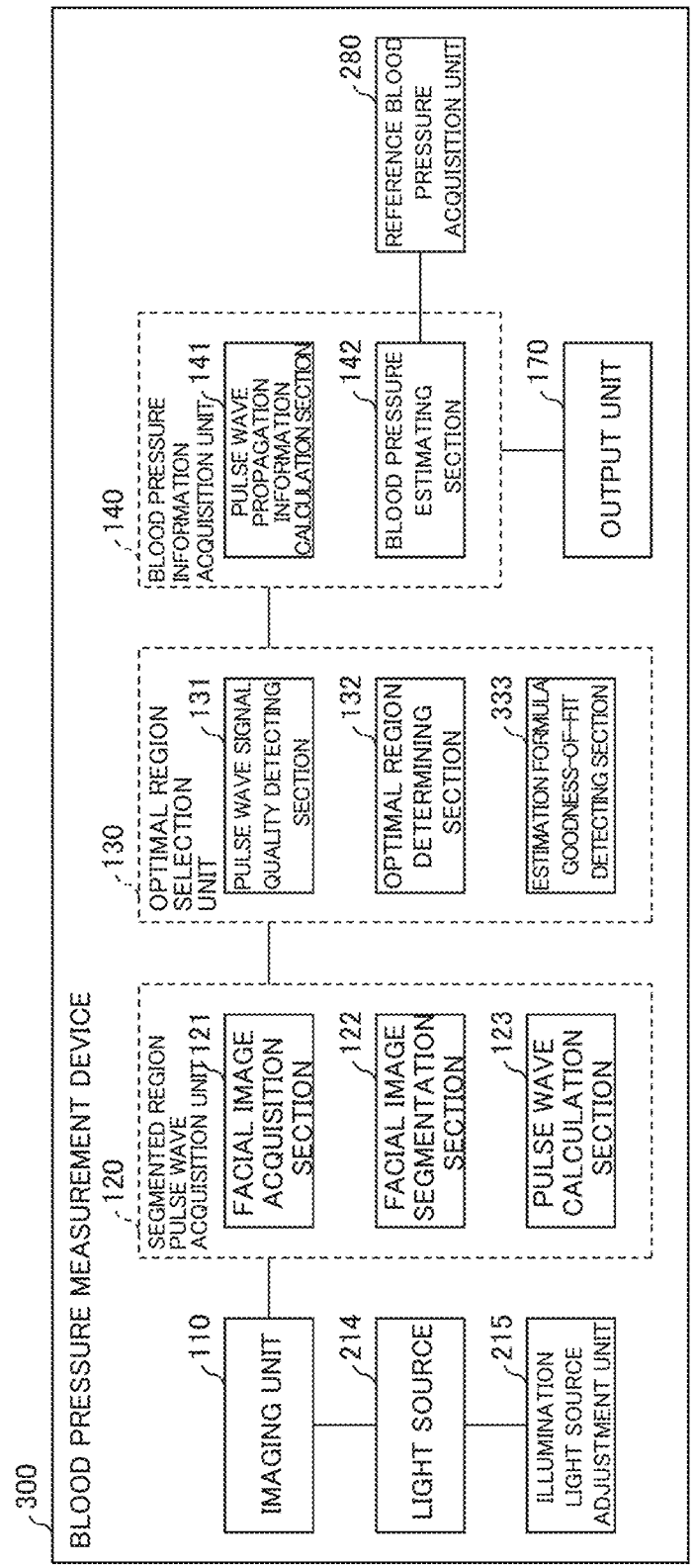
FIG. 11 is a block diagram illustrating a schematic constitution of a blood pressure measurement device 300 according to a third embodiment.

FIG. 11 is a block diagram illustrating a schematic constitution of a blood pressure measurement device 300 according to the third embodiment. As illustrated in FIG. 11, the blood pressure measurement device 300 is different in configuration from the second embodiment in that an optimal region selection unit 130 further includes an estimation formula goodness-of-fit detecting section 333.

The estimation formula goodness-of-fit detecting section 333 detects goodness of fit of the estimation formula created by a blood pressure estimating section 142 with respect to the measured blood pressure acquired by a reference blood pressure acquisition unit 280.

At the time of calibration in which an estimation formula is created with reference to the reference blood pressure, a plurality of specific areas in the facial image of the subject are each segmented into a plurality of regions by a facial image segmentation section 122, and then the blood pressure estimating section 142 creates an estimation formula for a combination of the regions between the areas.

Figure 12:
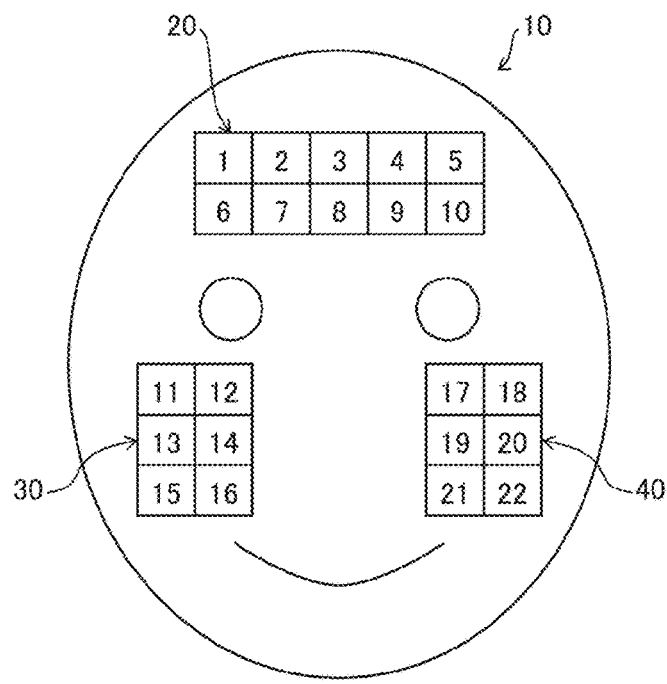
FIG. 12 is a diagram illustrating an example of an image of a face segmented into a plurality of regions.

A blood pressure information acquisition unit 140 calculates pulse wave propagation information between two regions for a plurality of region combinations by using the function of a pulse wave propagation information calculation section 141. FIG. 12 is a diagram illustrating an example of an image 10 of a face in which a plurality of specific areas are each segmented into a plurality of regions by the facial image segmentation section 122. As illustrated in FIG. 12, for example, in the case where a forehead area 20 is segmented into 10 regions, and left and right cheek areas 30, 40 are segmented together into 12 regions, the pulse wave propagation information calculation section 141 calculates the pulse wave propagation information for each of 120 region combinations (10×12).

The blood pressure estimating section 142 refers to the pulse wave propagation information calculated for the 120 combinations of the respective regions and the measured blood pressure acquired by the reference blood pressure acquisition unit 280, thereby creating 120 blood pressure estimation formulas.

Figure 13:
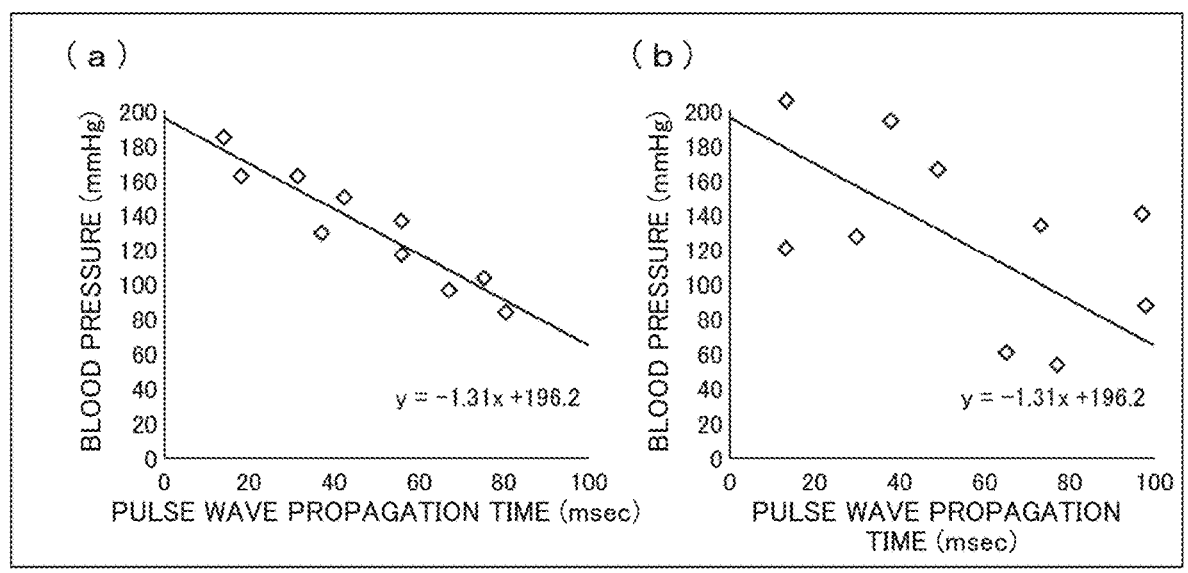
FIGS. 13($a$) and ($b$) are diagrams each illustrating an example of goodness of fit between an estimation formula and measured blood pressure.

The estimation formula goodness-of-fit detecting section 333 uses a freedom degree-adjusted coefficient of determination to evaluate the goodness of fit between the created estimation formula and the measured blood pressure. FIG. 13 is diagrams each illustrating an example of the goodness of fit between an estimation formula and measured blood pressure. In a graph of FIG. 13(a), since the estimation formula is well fitted to the measured blood pressure plotted with diamond marks, it is understood that the goodness of fit between the estimation formula and the measured blood pressure is high. On the other hand, in a graph of FIG. 13(b), it is understood that the goodness of fit between the estimation formula and the measured blood pressure is low because a difference between the estimation formula and the measured blood pressure is large.

FIGS. 14(a) and (b) are diagrams illustrating a relationship between estimated blood pressure and a fluctuation by a residual error relative to the mean blood pressure of the measured blood pressure. As illustrated in FIG. 14(a), when a measured blood pressure value is represented by y, an estimated blood pressure value is represented by $\hat{y}=ax+b$, and the mean value of the measured blood pressure values is represented by m, a difference between the measured blood pressure value y and the mean value m is divided into a portion by the estimated blood pressure value and a residual error, which is a remaining portion. Accordingly, the total fluctuation may be calculated from the sum of the fluctuation by the residual error and the fluctuation by the estimated blood pressure value.

Since a coefficient of determination used for evaluating the goodness of fit between the estimation formula and the measured blood pressure indicates a fluctuation rate that can be explained by the estimation formula in the total fluctuation, a coefficient of determination $R^2$ is calculated by an expression of "fluctuation by estimated blood pressure value"÷"total fluctuation".

The freedom degree-adjusted coefficient of determination may be calculated by dividing each fluctuation by the degree of freedom using a known method (reference page: http://www.geisya.or.jp/~mwm48961/statistics/coef_det1.htm).

FIG. 14(c) is a table illustrating rankings of optimal regions, based on the goodness of fit of the estimation formula created from the combinations of the segmented regions with respect to the measured blood pressure. As illustrated in FIG. 14(c), the estimation formula goodness-of-fit detecting section 333 calculates a plurality of estimation formulas of freedom degree-adjusted coefficients of determination created by the blood pressure estimating section 142, and ranks the goodness of fit of the estimation formula with respect to the measured blood pressure based on the freedom degree-adjusted coefficient of determination.

An optimal region determining section 132 selects the optimal region based on the goodness of fit of the estimation formula, ranked by the estimation formula goodness-of-fit detecting section 333, with respect to the measured value in addition to the pulse wave signal quality detected by the pulse wave signal quality detecting section 131. Specifically, the optimal region determining section 132 first extracts all of the region combinations in which the SNR of the pulse wave signal detected by the pulse wave signal quality detecting section 131 is equal to or greater than a certain threshold value (for example, 0.15). Next, the optimal region determining section 132 refers to the rankings of the goodness of fit of the estimation formulas between the respective regions, created by the estimation formula goodness-of-fit detecting section 333, with respect to the measured pressure to determine the combination of the highest ranking as an optimal region among the extracted region combinations.

Thus, the goodness of fit of the estimation formula with respect to the measured blood pressure is an index that represents how much the estimated blood pressure between the regions estimated by using the estimation formula is fitted (approximated) to the measured blood pressure, and is evaluated based on the coefficient of determination $R^2$.

According to these configurations, a region in which the pulse wave signal is acquired with higher accuracy than a fixed level of accuracy and the goodness of fit of the estimated blood pressure estimated by using the estimation formula is high with respect to the measured blood pressure, is determined to be the optimal region. Thus, it is possible to take into consideration personal differences of each measurement subject, such as positions of the blood vessels, facial contours, and the like, and select a region having a strong correlation with the measured blood pressure. This makes it possible to perform the blood pressure estimation while taking into consideration both the personal differences and the image capturing environment, and to estimate the blood pressure with high accuracy.

The optimal region determining section 132 makes the determination based on both the parameters of pulse wave signal quality and the goodness of fit of the estimation formula in the present embodiment, but may select the optimal region based on only any one of the indices.

In the above-described first to three embodiments, the region selection by the face is mainly explained. However, the region selection may be made by, in addition to the face, a region on the body surface of the subject where the pulse wave signal can be acquired, for example, a site such as the palm, arm, or sole; in this case, the region may include the neck when the region selection is made by using a facial image. The region selection is not limited to the configuration in which the pulse wave signal is acquired by using the facial image, and the biometric information including pulse waves may be acquired from a plurality of contact sensors brought into contact with and attached to the body surface of the subject such as the face, neck, palm, arm, sole, or the like.

Implementation Example by Software

Control blocks of the blood pressure measurement devices 100, 200, and 300 (in particular, the segmented region pulse wave acquisition unit 120, the optimal region selection unit 130, and the blood pressure information acquisition unit 140) may be implemented by logic circuits (hardware) formed in integrated circuits (IC chips) and the like, or may be implemented by software.

In the latter case, the blood pressure measurement devices 100, 200, and 300 are each provided with a computer configured to execute commands of a program, which is software for implementing each function. The stated computer includes at least one processor (control device), for example, and includes at least one computer-readable recording medium having stored the program therein. In the computer, the processor reads out the program from the recording medium and executes the program, thereby accomplishing the object of the present disclosure. For example, a Central Processing Unit (CPU) may be used as the processor. As the recording medium, a "non-transitory tangible medium" such as a tape, a disk, a card, a semiconductor memory, and a programmable logic circuit may be used in addition to a Read Only Memory (ROM). Additionally, a Random Access Memory (RAM) on which the program is loaded, or the like may be further provided. Further, the program may be supplied to the computer via any transmission medium (communication network, broadcast wave, or the like) capable of transmitting the program. Note that an aspect of the present disclosure may be implemented in a form of data signal set in a carrier wave, in which the above-mentioned program is embodied by electronic transmission.

Supplement

A blood pressure measurement device according to a first aspect of the present disclosure includes: a pulse wave acquisition unit configured to acquire a pulse wave from each of a plurality of regions on a body surface of a subject; a region selection unit configured to select at least two regions from among the plurality of regions in accordance with signal quality of the pulse wave of each region acquired by the pulse wave acquisition unit; and a blood pressure information acquisition unit configured to calculate blood pressure information with reference to pulse wave propagation information indicating pulse wave propagation between the at least two regions selected by the region selection unit.

With the above configuration, blood pressure may be measured with high accuracy.

A blood pressure measurement device according to a second aspect of the present disclosure may be configured such that, in the first aspect, the blood pressure information acquisition unit calculates the blood pressure information with reference to the pulse wave propagation information indicating the pulse wave propagation between the at least two regions and an amount of characteristics obtained from a pulse wave form obtained from at least one region.

With the above configuration, since the blood pressure information is calculated with reference to the pulse wave propagation information of the subject and the amount of characteristics, it is possible to measure the blood pressure with high accuracy.

A blood pressure measurement device according to a third aspect of the present disclosure may further include, in the first or second aspect, a measurement subject biometric parameter input unit configured to receive input of biometric parameters of the subject, where the blood pressure information acquisition unit may acquire blood pressure information with reference to a blood pressure estimation formula corresponding to the biometric parameters of the subject input to the measurement subject biometric parameter input unit and the at least two regions selected by the region selection unit.

With the above-described configuration, the blood pressure estimation may be performed in accordance with the biometric parameters of the subject, thereby making it possible to accurately measure the blood pressure.

A blood pressure measurement device according to a fourth aspect of the present disclosure may further include, in the first or second aspect, a reference blood pressure acquisition unit configured to acquire reference blood pressure of the subject, where the blood pressure information acquisition unit may acquire the blood pressure information with reference to the reference blood pressure of the subject acquired by the reference blood pressure acquisition unit.

With the above configuration, since the blood pressure information is acquired with reference to the reference blood pressure of the subject, it is possible to measure the blood pressure with high accuracy.

A blood pressure measurement device according to a fifth aspect of the present disclosure may be configured such that, in the first to fourth aspects, the pulse wave acquisition unit includes an imaging unit configured to capture an image of the subject, and the pulse wave acquisition unit segments the captured image of the subject into a plurality of regions and then calculates a pulse wave in each of the segmented regions with reference to the captured image.

The above-described configuration makes it possible to accurately measure the blood pressure from the image.

A blood pressure measurement device according to a sixth aspect of the present disclosure may further include, in the fifth aspect, an illumination light source adjustment unit configured to adjust light emission intensity of an illumination light source configured to emit illumination light for capturing the image by the imaging unit.

The above-described configuration makes it possible to accurately measure the blood pressure from the image even in different image capturing environments.

A blood pressure measurement device according to a seventh aspect of the present disclosure may be configured such that, in the first to sixth aspects, the pulse wave acquisition unit segments, for each of a plurality of specific areas previously set to the body surface of the subject, the specific area into a plurality of regions.

In the above configuration, since the specific area is segmented into the plurality of regions, the blood pressure may be measured with high accuracy.

A blood pressure measurement device according to an eighth aspect of the present disclosure may be configured such that the region selection unit extracts at least one region from each of a distal area and a proximal area in accordance with signal quality of each region.

According to the above configuration, since the region selection unit extracts at least one region from each of the distal area and the proximal area in accordance with signal quality of each region, the blood pressure may be measured with high accuracy.

A blood pressure measurement device according to a ninth aspect of the present disclosure may be configured such that, in the first to eighth aspects, the pulse wave acquisition unit segments, for each of the plurality of specific areas previously set to the body surface of the subject, the specific area into the plurality of regions; the blood pressure information acquisition unit calculates the pulse wave propagation information regarding combinations of the regions between the specific areas; and further provided is an estimation formula goodness-of-fit detecting section configured to detect goodness of fit of estimated blood pressure, which is estimated based on each of the pulse wave propagation information in the combinations of the regions between the specific areas, with respect to the measured blood pressure.

With the above configuration, the blood pressure may be measured accurately from the facial image in consideration of personal differences such as the positions of the blood vessels, the contours of the face, and the like of each measurement subject.

A blood pressure measurement device according to a tenth aspect of the present disclosure may be configured such that, in the first to ninth aspects, the blood pressure information acquisition unit further includes a storage configured to store the past estimated blood pressure, and an output unit configured to output the past estimated blood pressure values accumulated in the storage and the present estimated blood pressure values.

According to the above configuration, it is possible to perform the comparison with not only the blood pressure at the measurement time but also the blood pressure of the past, so that it is possible to grasp the fluctuations in blood pressure.

The blood pressure measurement device according to each of the aspects of the present disclosure may be implemented by a computer. In this case, a control program of the blood pressure measurement device configured to implement the blood pressure measurement device by the computer by causing the computer to function as constituent elements (software elements) provided in the blood pressure measurement device, and a computer-readable recording medium storing the control program therein also fall within the scope of the present disclosure.

The present disclosure is not limited to each of the above-described embodiments. It is possible to make various modifications within the scope of the claims. An embodiment obtained by appropriately combining technical elements each disclosed in different embodiments falls also within the technical scope of the present disclosure. Furthermore, technical elements disclosed in the respective embodiments may be combined to provide a new technical feature.

CROSS-REFERENCE TO RELATED APPLICATIONS

This application claims the benefit of priority to Japanese Patent Application Number 2017-240930 filed on Dec. 15, 2017. The entire contents of the above-identified application are hereby incorporated by reference.

REFERENCE SIGNS LIST 100, 200, 300 Blood pressure measurement device
110 Imaging unit
120 Segmented region pulse wave acquisition unit (pulse wave acquisition unit)
121 Facial image acquisition section
122 Facial image segmentation section
123 Pulse wave calculation section
130 Optimal region selection unit (region selection unit)
131 Pulse wave signal quality detecting section
132 Optimal region determining section
140 Blood pressure information acquisition unit
141 Pulse wave propagation information calculation section
142 Blood pressure estimating section
150 Measurement subject biometric parameter input unit
160 Database
170 Output unit
214 Light source
215 Illumination light source adjustment unit
280 Reference blood pressure acquisition unit
333 Estimation formula goodness-of-fit detecting section

The invention claimed is:

1. A blood pressure measurement device comprising:
a pulse wave acquisition unit configured to acquire a pulse wave from each of a plurality of regions on a body surface of a single site of a subject;
a region selection unit configured to select at least two regions from among the plurality of regions in accordance with signal quality of the pulse wave of each region acquired by the pulse wave acquisition unit;
a blood pressure information acquisition unit configured to calculate blood pressure information with reference to pulse wave propagation information indicating pulse wave propagation between the at least two regions selected by the region selection unit;
a measurement subject biometric parameter input unit configured to receive an input of biometric parameters of the subject; and
a database configured to store, for each of the biometric parameters, a blood pressure estimation formula between the at least two regions selected by the region selection unit,
wherein the blood pressure information acquisition unit selects, with reference to the biometric parameters input by the measurement subject biometric parameter input unit, one of the blood pressure estimation formulas to be used for calculating the blood pressure information, and calculates the blood pressure information using the selected blood pressure estimation formula.

2. The blood pressure measurement device according to claim 1,
wherein the blood pressure information acquisition unit calculates the blood pressure information with reference to the pulse wave propagation information indicating the pulse wave propagation between the at least two regions and an amount of characteristics obtained from a pulse wave form obtained from at least one region.

3. A blood pressure measurement device comprising:
a pulse wave acquisition unit configured to acquire a pulse wave from each of a plurality of regions on a body surface of a single site of a subject;
a region selection unit configured to select at least two regions from among the plurality of regions in accordance with signal quality of the pulse wave of each region acquired by the pulse wave acquisition unit;
a blood pressure information acquisition unit configured to calculate blood pressure information with reference to pulse wave propagation information indicating pulse wave propagation between the at least two regions selected by the region selection unit; and
a reference blood pressure acquisition unit configured to acquire reference blood pressure of the subject,
wherein the blood pressure information acquisition unit creates a blood pressure estimation formula corresponding to the subject, using the pulse wave propagation information and the reference blood pressure of the subject acquired by the reference blood pressure acquisition unit, and acquires the blood pressure information with reference to the created blood pressure estimation formula.

4. The blood pressure measurement device according to claim 1,
wherein the pulse wave acquisition unit includes an imaging unit configured to capture an image of the subject, and
the pulse wave acquisition unit segments the captured image of the subject into a plurality of regions, and then calculates a pulse wave in each of the segmented regions with reference to the captured image.

5. The blood pressure measurement device according to claim 4, further comprising:
an illumination light source adjustment unit configured to adjust light emission intensity of an illumination light source configured to emit illumination light for capturing the image by the imaging unit.

6. The blood pressure measurement device according to claim 1,
wherein the pulse wave acquisition unit segments, for each of a plurality of specific areas previously set to the body surface of the subject, the specific area into a plurality of regions.

7. The blood pressure measurement device according to claim 1,
wherein the region selection unit extracts at least one region from each of a distal area and a proximal area in accordance with signal quality of each region.

8. A blood pressure measurement device comprising:
a pulse wave acquisition unit configured to acquire a pulse wave from each of a plurality of regions on a body surface of a single site of a subject;
a region selection unit configured to select at least two regions from among the plurality of regions in accordance with signal quality of the pulse wave of each region acquired by the pulse wave acquisition unit; and
a blood pressure information acquisition unit configured to calculate blood pressure information with reference to pulse wave propagation information indicating pulse wave propagation between the at least two regions selected by the region selection unit, wherein the pulse wave acquisition unit segments, for each of the plurality of specific areas previously set to the body surface of the subject, the specific area into the plurality of regions, the blood pressure information acquisition unit calculates the pulse wave propagation information regarding combinations of the regions between the specific areas, and there is further provided an estimation formula goodness-of-fit detecting section configured to detect goodness of fit of estimated blood pressure, which is estimated based on each of the pulse wave propagation information in the combinations of the regions between the specific areas, with respect to the measured blood pressure.

9. The blood pressure measurement device according to claim 1, wherein the blood pressure information acquisition unit further includes a storage configured to store past estimated blood pressure, and an output unit configured to output the past estimated blood pressure values accumulated in the storage and present estimated blood pressure values.

10. A blood pressure measurement method comprising:

acquiring a pulse wave from each of a plurality of regions on a body surface of a single site of a subject;

selecting at least two regions from among the plurality of regions in accordance with signal quality of the pulse wave of each region acquired by the acquiring of the pulse wave;

acquiring blood pressure information in which the blood pressure information is calculated with reference to pulse wave propagation information indicating pulse wave propagation between the at least two regions selected by the selecting of the at least two regions;

receiving an input of biometric parameters of the subject; and storing, for each of the biometric parameters, a blood pressure estimation formula between the selected at least two regions, wherein acquiring the blood pressure information includes selecting, with reference to the input biometric parameters, one of the blood pressure estimation formulas to be used for calculating the blood pressure information, and calculating the blood pressure information using the selected blood pressure estimation formula.

11. The blood pressure measurement device according to claim 2, further comprising:

a reference blood pressure acquisition unit configured to acquire reference blood pressure of the subject, wherein the blood pressure information acquisition unit acquires the blood pressure information with reference to the reference blood pressure of the subject acquired by the reference blood pressure acquisition unit.

12. The blood pressure measurement device according to claim 2, wherein the pulse wave acquisition unit includes an imaging unit configured to capture an image of the subject, and the pulse wave acquisition unit segments the captured image of the subject into a plurality of regions, and then calculates a pulse wave in each of the segmented regions with reference to the captured image.

13. The blood pressure measurement device according to claim 3, wherein the pulse wave acquisition unit includes an imaging unit configured to capture an image of the subject, and the pulse wave acquisition unit segments the captured image of the subject into a plurality of regions, and then calculates a pulse wave in each of the segmented regions with reference to the captured image.

14. The blood pressure measurement device according to claim 11, wherein the pulse wave acquisition unit includes an imaging unit configured to capture an image of the subject, and the pulse wave acquisition unit segments the captured image of the subject into a plurality of regions, and then calculates a pulse wave in each of the segmented regions with reference to the captured image.

* * * * *